(12) United States Patent
Dohmen et al.

(10) Patent No.: US 12,722,000 B2
(45) Date of Patent: Sep. 1, 2026

(54) IMPLANTABLE CARDIAC ELECTRODE

(71) Applicant: BIOTRONIK SE & Co. KG, Berlin (DE)

(72) Inventors: Daniel Dohmen, San Francisco, CA (US); Zhen Fu Timothy Bay, Singapore (SG); Dun Kai Koh, Singapore (SG); Qi Zhao Jensen Mong, Singapore (SG); Wee Ping Yeo, Singapore (SG); Yanling Li, Singapore (SG); Qiong Wu, Singapore (SG)

(73) Assignee: BIOTRONIK SE & Co. KG, Berlin (DE)

( * ) Notice: Subject to any disclaimer, the term of this patent is extended or adjusted under 35 U.S.C. 154(b) by 293 days.

(21) Appl. No.: 18/580,685

(22) PCT Filed: Jun. 10, 2022

(86) PCT No.: PCT/EP2022/065786
§ 371 (c)(1),
(2) Date: Jan. 19, 2024

(87) PCT Pub. No.: WO2023/001455
PCT Pub. Date: Jan. 26, 2023

(65) Prior Publication Data

US 2024/0366933 A1 Nov. 7, 2024

(30) Foreign Application Priority Data

Jul. 19, 2021 (EP) .................................... 21186330

(51) Int. Cl.
*A61N 1/05* (2006.01)
*B29C 65/16* (2006.01)
(Continued)

(52) U.S. Cl.
CPC ........ *A61N 1/0573* (2013.01); *B29C 65/1635* (2013.01); *B29K 2021/003* (2013.01);
(Continued)

(58) Field of Classification Search
CPC .............. A61N 1/0573; B29C 65/1635; B29C 65/1616; B29C 66/12821; B29C 66/1284;
(Continued)

(56) References Cited

U.S. PATENT DOCUMENTS 7,092,766 B1 * 8/2006 Salys .................. A61N 1/0565 607/128
2010/0030192 A1 2/2010 Gunderson et al.
(Continued)

FOREIGN PATENT DOCUMENTS

JP 2016187835 A 11/2016
WO 2016092208 A1 6/2016

OTHER PUBLICATIONS

International Search Report (PCT/ISA/210) and Written Opinion mailed on Aug. 31, 2022, by the European Patent Office as the International Searching Authority for International Application No. PCT/EP2022/065786. (10 pages).

*Primary Examiner* — Paula J Stice
(74) *Attorney, Agent, or Firm* — Buchanan Ingersoll & Rooney PC

(57) ABSTRACT

An implantable cardiac electrode comprising an electrode lead and an electrode tip, wherein the electrode tip comprises a housing and a fixation screw received within the housing, wherein the fixation screw is electrically conductive connected to the electrode lead and serves for fixing the electrode tip within cardiac tissue. The housing comprises a first element and a second element, wherein the first element has a sleeve-like shape and defines a receiving space for the fixation screw, wherein the second element is at least par-
(Continued)

tially inserted into the receiving space so that the first element overlaps the second element in an overlapping area, wherein the first element and the second element are bonded together in the overlapping area, wherein the first element comprises a first material being transparent for light having a first wavelength, wherein the second element comprises a second material that is absorbing for light having the first wavelength.

12 Claims, 1 Drawing Sheet

(51) Int. Cl.

| | |
|---|---|
| *B29K 21/00* | (2006.01) |
| *B29K 67/00* | (2006.01) |
| *B29K 71/00* | (2006.01) |
| *B29K 75/00* | (2006.01) |
| *B29K 105/00* | (2006.01) |
| *B29L 31/00* | (2006.01) |

(52) U.S. Cl.
CPC .... *B29K 2067/003* (2013.01); *B29K 2071/00* (2013.01); *B29K 2075/00* (2013.01); *B29K 2105/0085* (2013.01); *B29K 2995/0026* (2013.01); *B29L 2031/753* (2013.01)

(58) Field of Classification Search
CPC ... B29C 66/5344; B29C 66/71; B29C 66/712; B29C 66/7332; B29C 66/73921; B29K 2021/003; B29K 2067/003; B29K 2071/00; B29K 2075/00; B29K 2105/0085; B29K 2995/0026; B29L 2031/753
See application file for complete search history.

(56) References Cited

U.S. PATENT DOCUMENTS

| | | | | |
|---|---|---|---|---|
| 2010/0305672 | A1* | 12/2010 | Felling ................. | A61N 1/0573 607/116 |
| 2011/0009939 | A1* | 1/2011 | Foster .................. | A61N 1/0573 607/127 |
| 2011/0270356 | A1* | 11/2011 | McKenzie .............. | B32B 27/36 607/57 |
| 2012/0203317 | A1* | 8/2012 | Valentine ............... | A61N 1/375 607/116 |
| 2013/0192751 | A1* | 8/2013 | Arai .................. | B29C 66/30325 156/272.8 |
| 2014/0243946 | A1 | 8/2014 | Zhang et al. | |
| 2015/0239225 | A1 | 8/2015 | Helmer et al. | |

* cited by examiner

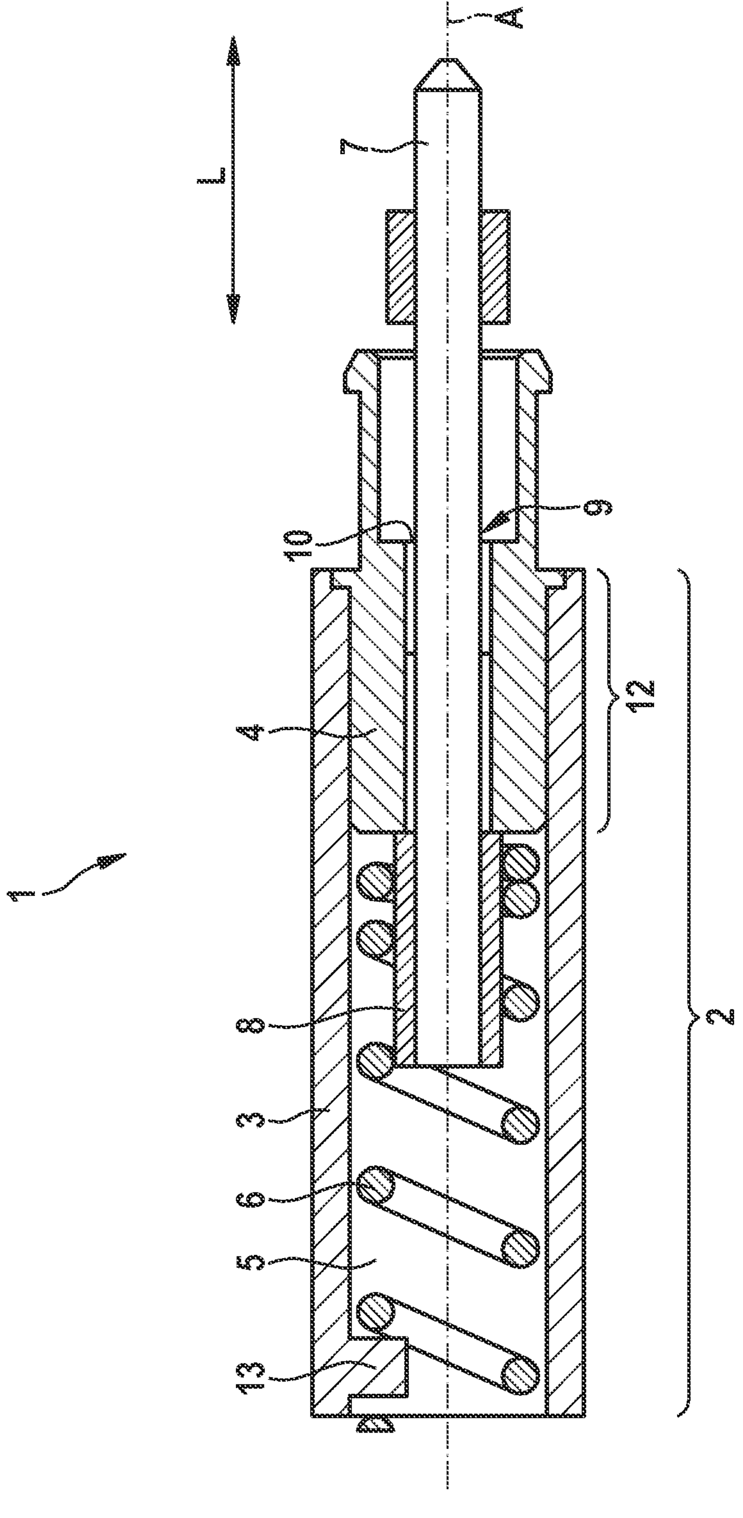
A
L
7
9
10
12
4
1
2
8
3
6
5
13

IMPLANTABLE CARDIAC ELECTRODE

CROSS-REFERENCE TO RELATED APPLICATIONS

This application is the United States National Phase under 35 U.S.C. § 371 of PCT International Patent Application No. PCT/EP2022/065786, filed on Jun. 10, 2022, which claims the benefit of European Patent Application No. 21186330.3, filed on Jul. 19, 2021, the disclosures of which are hereby incorporated by reference herein in their entireties.

TECHNICAL FIELD

The present invention relates to an implantable cardiac electrode according to the preamble of claim 1 and to a method for manufacturing such an electrode according to the preamble of claim 11.

BACKGROUND

U.S. Publication No. 2011/0270356 A1 describes an implantable component and a polymeric hermetic encapsulation disposed around the component. The component and the encapsulation have one or more plasma-activated surfaces directly bonded to one another. This bonding can be performed by laser welding. During laser welding, a laser beam is directed towards the overlapping polymer surfaces. The first polymer surface contacted by the laser beam allows the irradiation to pass through with a degree of transparency (the "transparent polymer surface"). Meanwhile, the second polymer surface contacted by the laser beam absorbs the irradiation due to the presence of one or more absorbing media therein or due to other modifications or characteristics thereof (the "absorbent polymer surface"). The irradiation absorbed by the absorbent polymer surface, combined with any irradiation absorbed by the transparent polymer surface, produces localized heating in the vicinity of the weld leading to melting and bonding of the polymer surfaces at the interface.

International Publication No. WO 2016/092208 A1 describes a first element comprising a first portion suitable for being welded to a second portion of a second element by applying a laser beam. The first portion is transparent for the laser beam and the second portion is absorbent for the laser beam. This international patent application further describes a composition from which these elements can be manufactured. Furthermore, it describes the use of this composition in the medical field, in particular the manufacture of catheters and parts of medical equipment, in the welding of automobile tubes, in particular connectors for automobile tubes, and for sports shoes.

U.S. Publication No. 2015/0239225 A1 describes a method of welding two parts of a medical device. A first part having an internal surface with a provided welding seam and a second part having a joining portion comprising an external surface with an opposite welding seam are provided. At least one of the first and the second part has one or more tensioning members that are configured to interact with the surface of the other one of the first and second part to create a normal force between the welding seam of the first part and opposite welding seam of the second part. The laser welding can be carried out such that a top part is transparent to a laser beam and that a bottom part can be either transparent or opaque to the laser beam.

U.S. Publication No. 2010/0030192 A1 describes a catheter shaft bond arrangement including a first catheter shaft defining a first lumen, a second catheter shaft defining a second lumen, and a first bonding member. The first bonding member is configured to bond with the first and second catheter shafts to create a molded bond upon application of heat to the first bonding member. This heat can be applied by laser welding, wherein transparent and absorbing polymer parts are bonded together. The laser beam penetrates the transparent polymer and is converted to heat in the colored/absorbing polymer. Since both of the polymer parts are pressed together during the welding process, heat is conducted from the colored/absorbing polymer to the transparent polymer, allowing both materials to flow and create a heat-generated bond.

Thus, there exit different laser welding technologies that are partly applied in the field of medical devices, in particular in the manufacture of catheters.

Electrode tips of implantable cardiac electrodes regularly comprise metal parts in their distal end region. These metal parts are difficult and expensive to manufacture. In addition, they limit the degrees of freedom when designing an electrode tip.

There also exist different techniques to join different plastic parts. However, these techniques—like screwing, clamping or gluing-typically require a complex geometry of the parts to be joined together or additional components like rings or adhesives. These requirements make the manufacturing process of corresponding joint elements quite costly and time-consuming.

The present disclosure is directed toward overcoming one or more of the above-mentioned problems, though not necessarily limited to embodiments that do.

SUMMARY

It is an object of the present invention to provide a cardiac electrode having an improved performance and/or being easier and cheaper to produce than cardiac electrodes known from prior art.

At least this object is achieved with an implantable cardiac electrode having the claim elements of claim 1. Such an electrode comprises an electrode lead and an electrode tip. The electrode tip comprises a housing and a fixation screw received within the housing. The fixation screw is connected to the electrode lead in an electrically conductive manner. It serves for fixing the electrode tip within cardiac tissue of the patient to whom the implantable cardiac electrode is implanted.

According to an aspect of the present invention, the housing comprises a first element and a second element. The first element has a sleeve-like shape and defines a receiving space for the fixation screw. The second element is at least partially inserted into the receiving space. Consequently, the first element at least partially overlaps the second element. To be more precise, the first element overlaps the second element in an overlapping area or overlapping zone. In this context, the first element and the second element are bonded together in the overlapping area. This serves for a tight connection between the first element and the second element. The overlapping area can also be denoted as bonding area.

The first element comprises at least in the overlapping area a first material being transparent for light having a first wavelength. The second element comprises at least in the overlapping area a second material that is absorbing for light having the first wavelength. The combination of the first material being transparent for light of a specific wavelength and the second material being absorbing for light having the same wavelength allows joining the two elements without using any adhesive and without requiring a complex design of the elements.

Prior art solutions for joining two plastic components (in particular components made from polyether ether ketone, PEEK) encompass screw joints, clamping the components with rings, gluing the components with an adhesive, or welding the components by ultrasonic welding. However, these techniques have severe disadvantages since they are more complex than the manufacturing process necessary for manufacturing the presently claimed implantable cardiac electrode and typically require longer process times. Thus, the use of the first material for the first element and the second material for the second element enables a bonding technology that does neither require additional components like rings or adhesives nor complex geometries of the parts to be bonded (such as in case of a screw thread). This does not only reduce time and cost for manufacturing the implantable cardiac electrode but also increases the freedom in designing the implantable cardiac electrode.

The presently claimed implantable cardiac electrode has a functional and cost-effective design and can be easily produced in an automated way. It offers a designer more degrees of freedom in the development of new variations of the general design of the presently claimed implantable cardiac electrode. The use of the first transparent material and the second absorbing material eliminates the need of an additional cleaning process after having bonded together the first element and the second element like after gluing two parts together. Furthermore, due to this design, the bonding between the first element and the second element can be realized by laser welding. This creates a very high bonding strength between the first element and the second element.

The first element and the second element replace metal components that are typically used in electrode tips of implantable cardiac electrodes. These metal parts are rather expensive and are typically used in the form of half shells. In contrast, the first element has a sleeve-like shape, i.e., it fully surrounds the receiving space for the fixation screw. Furthermore, the second element is a single element not being composed of half shells. Consequently, the number of individual parts for making up the housing of the electrode tip is significantly reduced with respect to prior art solutions. The more individual parts are used, the higher is the number of weaknesses in the resulting component. Thus, by changing the design of the electrode tip such that the number of individual components is reduced, the amount of potential weaknesses is also reduced. This enhances the stability and reliability of the electrode tip and accordingly of the whole implantable cardiac electrode.

Expressed in other words, making use of the sleeve-like shape of the first element instead of half shells according to prior art solutions is one reason why the stability of the electrode tip is significantly increased.

The term "transparent for light" is to be interpreted such that at least 75%, in particular at least 80%, in particular at least 85%, in particular at least 90%, in particular at least 95%, in particular at least 97%, in particular at least 98%, in particular at least 99%, in particular 100% of the irradiated light can pass through the first material. The term "absorbing for light" is to be interpreted such that at least 75%, in particular at least 80%, in particular at least 85%, in particular at least 90%, in particular at least 95%, in particular at least 97%, in particular at least 98%, in particular at least 99%, in particular 100% of the irradiated light cannot pass through the second material.

In an embodiment, the implantable cardiac electrode can also be denoted as an electrode that can be actively fixed. Typically, the fixation screw is turned like a screwdriver into the cardiac tissue of the patient at the desired implantation site. For this purpose, a radial and axial movement of the fixation screw is necessary.

In an embodiment, the first element consists of the first material at least in the overlapping area. In an embodiment, the first element entirely consists of the first material. In an embodiment, the second element consists of the second material at least in the overlapping area. In an embodiment, the second element consists entirely of the second material.

The first wavelength can be generally any wavelength. Particularly appropriate wavelengths are wavelengths lying between the UV range and the near infrared range, in particular in a wavelength range of from 200 nm to 1000 nm, in particular of from 300 nm to 900 nm, in particular of from 400 nm to 800 nm, in particular of from 500 nm to 700 nm.

A particularly appropriate wavelength range is a wavelength range of from 600 nm to 1000 nm. In an embodiment, the first wavelength is, therefore, a wavelength lying in a range of from 600 nm to 1000 nm, in particular of from 650 nm to 950 nm, in particular of from 700 nm to 900 nm, in particular of from 750 nm to 850 nm, in particular of from 775 nm to 825 nm. A wavelength at or around 800 nm is particularly appropriate.

In an embodiment, the housing has a distal end at which the fixation screw can exit the receiving space in order to get anchored within cardiac tissue. The housing furthermore has a proximal end that is located opposite the distal end in a longitudinal extension direction of the housing. In this embodiment, the second element is at least partially inserted into the receiving space at the proximal end. To give an example, the second element can have the shape of a plug and can thus be used to at least partially close the proximal end of the receiving space and thus of the housing. Typically, the second element is designed such to offer the possibility for the electrode lead to be guided through the second element. Thus, even if the second element has the shape of a plug, it typically allows a guidance of the electrode lead through the second element into the receiving space for the fixation screw.

In an embodiment, the second element comprises a central bore through which the electrode lead is guided from an outside of the housing into the receiving space. Such a central bore is particularly appropriate for a uniform force application onto the electrode lead, thus allowing a particular appropriate sealing between the electrode lead and the second element. In an embodiment, the second element comprises a sealing element arranged between an inner side of the central bore and an outside of the electrode lead guided through the central bore.

In an embodiment, a connecting sleeve is located around the electrode lead in a distal electrode lead section located within the receiving space distally of the distal end of the second element. The connecting sleeve typically extends along the whole circumference of the electrode lead. The connecting sleeve serves for a connection between the electrode lead and the fixation screw in an electrically conductive manner.

In an embodiment, the first element comprises a protrusion that radially protrudes from an inner wall of the first element into the receiving space. The protrusion controls an axial movement of the fixation screw along a longitudinal axis extending along a longitudinal extension direction of the housing. The protrusion enables a radial movement of the fixation screw around the longitudinal axis so that the screw can get anchored in cardiac tissue. The protrusion is an integral part of the first element.

In an embodiment, the first material and the second material are thermoplastic materials. Though they can belong to the same group of thermoplastics, they necessarily exhibit different properties with respect to transparency, as outlined above.

In an embodiment, the first material and the second material are independently chosen from the group consisting of polyether ether ketones (PEEK), thermoplastic elastomers (TPE), thermoplastic polyurethanes (TPU), polyethylene terephthalate (PET), fluoropolymers, and copolymers of the precedingly mentioned polymers. In an embodiment, both the first material and the second material are materials belonging to the same group of materials, such as PEEK or TPE.

In an embodiment, the first material is a naturally colored PEEK. Such naturally colored PEEK is transparent for light in the wavelength range of from 750 nm to 850 nm, in particular of from 775 nm to 825 nm, in particular of from 790 nm to 810 nm.

In an embodiment, the second material is a black PEEK. Such a black PEEK is absorbing for light in the wavelength range of from 750 nm to 850 nm, in particular of from 775 nm to 825 nm, in particular of from 790 nm to 810 nm.

In an embodiment, the electrode lead is a bipolar electrode lead having a first electric conductor and a second electric conductor that are insulated against each other. The first electric conductor serves for electrically contacting the fixation screw, thus enabling the fixation screw to act as first electrode pole. The second electric conductor is brought into electric contact with a second electrode pole that is typically arranged in a distal end region of the housing around the outer circumference of the housing in a sleeve-like manner. The electrical contact between the second electric conductor and the second electrode pole can be realized along an appropriate electric path.

In an aspect, the present invention relates to a method for manufacturing an implantable cardiac electrode according to the preceding explanations. Such manufacturing method comprises the steps explained the following.

In a first step, a first element having a sleeve-like shape and defining a receiving space for a fixation screw is provided.

Furthermore, a fixation screw and an electrode lead being electrically coupled to the fixation screw are placed within the receiving space. This can be done in individual method steps or in a combined method step.

In another step, a second element is at least partially inserted into the receiving space of the first element so that the first element overlaps the second element in an overlapping area. The first element comprises at least in the overlapping area a first material being transparent for light having a first wavelength. At the same time, the second element comprises at least in the overlapping area a second material that is absorbing for light having the first wavelength.

In a further method step, the first element and the second element are bonded together in the overlapping area. This is done by laser welding and results in the formation of a housing of the electrode tip of the implantable cardiac electrode. This housing serves for receiving the fixation screw and a part of the electrode lead. The housing forms part of the electrode tip of the implantable cardiac electrode. In contrast to prior art designs, the first element and the second element can be made from a plastic material so that no metal components are any longer necessary for forming the electrode tip.

These method steps need not necessarily be done in the described sequence. Rather, any desired and sensible sequence of the individual method steps is possible.

Laser welding used for bonding together the first element and the second element is a very clean process that does not require any additional components or elements like in the case of clamping or gluing connections. In contrast to ultrasonic welding, it does not impart any components such as the electrode lead, located in an interior of the second element since the laser beam used for this laser welding is absorbed by the second material and consequently does not pass through the second material. Therefore, only a local heating at a surface of the second material is affected by the application of the laser beam upon laser welding.

In an embodiment, the laser welding is carried out as spot welding or as scan welding. By spot welding, individual welding spots are produced that serve for a bonding between the first element and the second element. The individual welding spots can be arranged as desired and needed for a tight bonding connection between the first element and the second element. Scan welding is a technique by which a welding seam is produced. Such a welding seam typically enables an even tighter connection between the first element and the second element than individual welding spots.

In an embodiment, the laser welding is carried out as scan welding with an exposition time lying in a range of from 10 seconds to 20 seconds, in particular of from 12 seconds to 18 seconds, in particular of from 14 seconds to 16 seconds. The exposition time is the time during which the laser beam is applied to the materials to be bonded together, i.e., to the first material and the second material. During the exposition time, the laser beam is moved along a trajectory defining the welding seam to be produced between the first material and the second material.

As already explained above, laser welding is a particularly clean process. Therefore, in an embodiment, the implantable cardiac electrode is further processed without additional cleaning step of the housing after having bonded together the first element and the second element. Whereas such additional cleaning step is necessary after having glued together individual components of the housing of the electrode tip in order to remove superfluous adhesive remainders, no such cleaning step is necessary for removing undesired components after having bonded the first element and the second element by laser welding. Of course, regular cleaning or contamination steps can be performed during the manufacture of the whole implantable cardiac electrode. In particular, a final cleaning, rinsing and/or sterilization is still possible and regularly necessary in order to comply with the relevant legal stipulations. But since the bonding between the first element and the second element can be done in such a clean manner that no additional cleaning step is necessary, the overall time and costs needed for producing the implantable cardiac electrode are reduced with respect to prior art manufacturing methods.

All embodiments explained with respect to the implantable cardiac electrode can be combined in any desired manner and can be transferred either individually or in any arbitrary combination to the described method. Likewise, all embodiments of the described method can be combined in any desired way and can be transferred either individually or in any arbitrary combination to the described implantable cardiac electrode.

Additional features, aspects, objects, advantages, and possible applications of the present disclosure will become apparent from a study of the exemplary embodiments and examples described below, in combination with the Figures and the appended claims.

BRIEF DESCRIPTION OF THE DRAWINGS

Further details of aspects of the present invention will be explained in the following with respect to an exemplary embodiment and an accompanying FIGURE. In the FIGURE:

FIG. 1 is a schematic longitudinal section through an electrode tip of an embodiment of an implantable cardiac electrode.

DETAILED DESCRIPTION

FIG. 1 shows a longitudinal section through an electrode tip 1 of an implantable cardiac electrode. The electrode tip 1 comprises a housing 2 defined by a sleeve 3 serving as first element and a plug 4 serving as second element. The housing extends along a longitudinal extension direction L and comprises a longitudinal axis A.

The sleeve 3 defines a receiving space 5 in its interior. The receiving space 5 serves for housing a fixation screw 6. The fixation screw 6 is intended to be turned into and thus anchored within cardiac tissue of a patient to whom the implantable cardiac electrode is to be implanted. The fixation screw 6 serves as first electrode pole. For this purpose, it is connected to an electrode lead 7 via an electrically conductive connecting sleeve 8.

The electrode lead 7 is guided from an exterior of the housing 2 into the receiving space 5 through a central bore 9 of the plug 4. To enable a tight connection between the plug 4 and the electrode lead 7, a sealing material 10 is arranged between an interior wall of the central bore 9 and an outer circumference of the electrode lead 7.

The plug 4 serves for closing a proximal end of the receiving space 5. The distal end of the receiving space 5 is open so as to allow the fixation screw 6 to exit the receiving space 5 and to contact the cardiac tissue in which it is to be anchored.

In an overlapping area 12, the sleeve 3 overlaps the plug 4. The sleeve 3 is made from naturally colored PEEK, i.e., a material being transparent for light having a wavelength of around 800 nm. The plug 4 is made from black PEEK, i.e., from a material that is non-transparent or absorbing for light having a wavelength of around 800 nm.

The sleeve 3 comprises a protrusion 13 extending from an inner wall of the sleeve 3 into the receiving space 5 towards the longitudinal axis A in a radial manner. This protrusion 13 controls an axial movement of the fixation screw 6 along the longitudinal axis A and allows a rotation of the fixation screw 6 about the longitudinal axis A.

Upon manufacturing the electrode tip 1, the plug 4 is inserted into the receiving space 5 defined by the sleeve 3 so that the overlapping area 12 between the sleeve 3 and the plug 4 is established. Afterwards, a laser beam having a wavelength of around 800 nm is used to introduce a welding seam between the sleeve 3 and the plug 4 by laser scan welding. For this purpose, the laser beam penetrates the sleeve 3 since it is transparent for the laser light of the laser beam. However, the laser beam is absorbed by the material of the plug 4. This absorption leads to a local heating of the contact area between the sleeve 3 and the plug 4, resulting in a bonding between the sleeve 3 and the plug 4 after cooling. Then, a very tight and clean connection between the sleeve 3 and the plug 4 is realized.

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range, including the end points.

The invention claimed is:

1. Implantable cardiac electrode comprising an electrode lead and an electrode tip, wherein the electrode tip comprises a housing and a fixation screw received within the housing, wherein the fixation screw is electrically conductive connected to the electrode lead and serves for fixing the electrode tip within cardiac tissue, wherein the housing comprises a first element and a second element, wherein the first element has a sleeve-like shape and defines a receiving space for the fixation screw, wherein the second element is at least partially inserted into the receiving space so that the first element overlaps the second element in an overlapping area, wherein the first element and the second element are bonded together in the overlapping area, wherein the first element comprises at least in the overlapping area a first material being transparent for light having a first wavelength, wherein the second element comprises at least in the overlapping area a second material that is absorbing for light having the first wavelength, wherein a connecting sleeved is arrange around the electrode lead and the fixation screw is arranged around the connecting sleeve.

2. Implantable cardiac electrode according to claim 1, wherein the first wavelength is a wavelength lying in a range of from 600 nm to 1000 nm.

3. Implantable cardiac electrode according to claim 1, wherein the housing has a distal end at which the fixation screw exits the receiving space and a proximal end located opposite the distal end in a longitudinal extension direction of the housing, wherein the second element is at least partially inserted into the receiving space at the proximal end.

4. Implantable cardiac electrode according to claim 1, wherein the second element comprises a central bore through which the electrode lead is guided from an outside of the housing into the receiving space.

5. Implantable cardiac electrode according to claim 1, wherein the first element comprises a protrusion radially protruding from a wall of the first element into the receiving space, wherein the protrusion controls an axial movement of the fixation screw along a longitudinal axis extending along a longitudinal extension direction of the housing, wherein the protrusion does not limit a radial movement of the fixation screw around the longitudinal axis.

6. Implantable cardiac electrode according to claim 1, wherein the first material and the second material are thermoplastics.

7. Implantable cardiac electrode according to claim 1, wherein the first material and second material are independently chosen from the group consisting of polyether ether ketones, thermoplastic elastomers, thermoplastic polyurethanes, polyethylene terephthalate, fluoropolymers, and copolymers thereof.

8. Implantable cardiac electrode according to claim 1, wherein the first material is a naturally colored polyether ether ketone.

9. Implantable cardiac electrode according to claim 1, wherein the second material is a black polyether ether ketone.

10. Method for manufacturing an implantable cardiac electrode according to claim 1, comprising the following steps:

a) providing a first element having a sleeve-like shape and defining a receiving space for a fixation screw;

b) placing a fixation screw and an electrode lead electrically coupled to the fixation screw within the receiving space;

c) at least partially inserting a second element into the receiving space so that the first element overlaps the second element in an overlapping area, wherein the first element comprises at least in the overlapping area a first material being transparent for light having a first wavelength, wherein the second element comprises at least in the overlapping area a second material that is absorbing for light having the first wavelength;

d) bonding together the first element and the second element in the overlapping area by laser welding so as to form a housing of an electrode tip of the implantable cardiac electrode.

11. Method according to claim 10, wherein the laser welding is carried out as spot welding or as scan welding.

12. Method according to claim 10, wherein the laser welding is carried out as scan welding with an exposition time lying in a range of from 10 s to 20 s.

* * * * *